United States Patent [19]

Murry et al.

[11] 4,189,286
[45] Feb. 19, 1980

[54] PERISTALTIC PUMP

[75] Inventors: Edward J. Murry, Palos Park; Joseph F. Brumbach, Niles, both of Ill.

[73] Assignee: Fibra-Sonics, Inc., Chicago, Ill.

[21] Appl. No.: 887,717

[22] Filed: Mar. 17, 1978

Related U.S. Application Data

[62] Division of Ser. No. 777,582, Mar. 15, 1977.

[51] Int. Cl.$^2$ ............................................. F04B 43/12
[52] U.S. Cl. ................................................... 417/477
[58] Field of Search ........................ 417/477, 476, 475

[56] References Cited

U.S. PATENT DOCUMENTS

| 3,011,684 | 12/1961 | Corneil | 417/477 |
|---|---|---|---|
| 3,737,257 | 6/1973 | DeVries | 417/477 |
| 3,756,752 | 9/1973 | Stenner | 417/477 |
| 4,025,241 | 5/1977 | Clemens | 417/477 |
| 4,113,409 | 9/1978 | Rossman et al. | 417/477 |

FOREIGN PATENT DOCUMENTS

| 2278952 | 2/1976 | France | 417/477 |
|---|---|---|---|
| 117110 | 7/1918 | United Kingdom | 417/477 |

*Primary Examiner*—Richard E. Gluck
*Attorney, Agent, or Firm*—Hill, Van Santen, Steadman, Chiara & Simpson

[57] ABSTRACT

An improved peristaltic pump which provides for rotating the head an offset angle relative to the rotor center and which includes a pivoted housing structure that can be adjusted by a spring loaded set screw so as to vary the quantity of material pump. By adjusting the set screw, the spacing between the head and the rotor can be adjusted to vary the volume of the pump. A one-way clutch assures that fluid cannot be supplied in a reversed direction through the pump.

2 Claims, 3 Drawing Figures

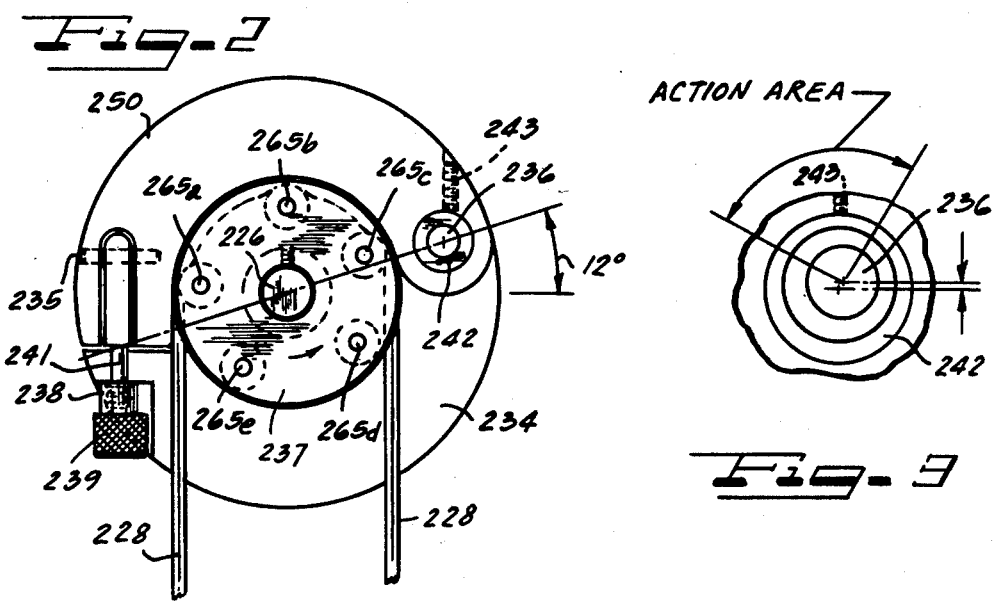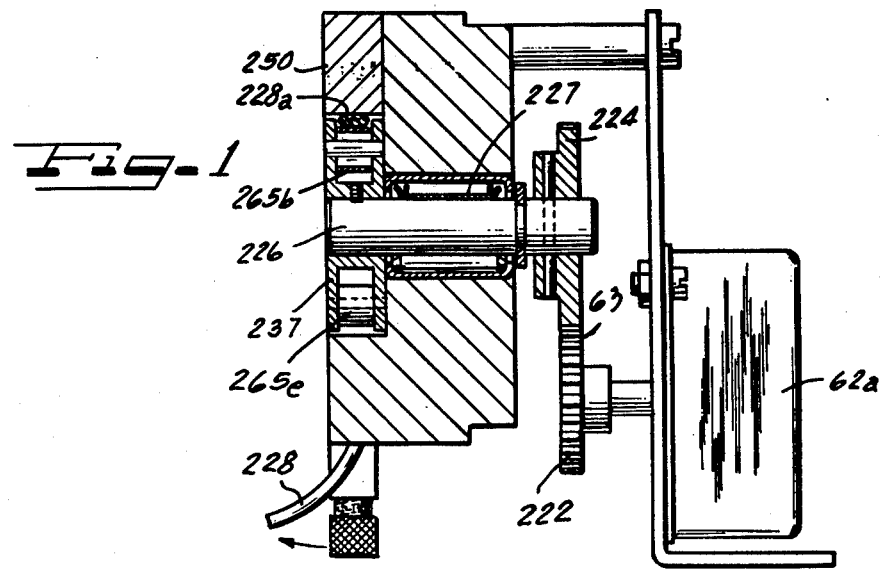

PERISTALTIC PUMP

This is a division of application Ser. No. 777,582, filed Mar. 15, 1977.

BACKGROUND OF THE INVENTION

1. Field of the Invention

This invention relates in general to a peristaltic pump.

2. Description of the Prior Art

Peristaltic pumps are known in the prior art, however, the present invention comprises an improved peristaltic pump that allows the volume supplied by the pump to be varied.

SUMMARY OF THE INVENTION

This invention relates to an improved peristaltic pump in which the rotor is driven by a one-way clutch and wherein the housing surrounding the rotor is offset by an angle and wherein the head spacing between the rotor and the clamping head is adjustable. The contact point of the head is offset relative to the diameter and rotor center as, for example, by an angle of 12° and the head spacing can be adjusted with a spring loaded set screw.

BRIEF DESCRIPTION OF THE DRAWINGS

FIG. 1 is a sectional drawing of the unique peristaltic pump and motor anti-reversal system;

FIG. 2 is another view of the peristaltic pump showing rollers and spring lock; and FIG. 3 is another view of the offset and camming of the peristaltic pump.

DESCRIPTION OF THE PREFERRED EMBODIMENTS

The unique floating peristaltic pump 46 is illustrated in FIGS. 1, 2 and 3. In FIG. 1, the motor 62a has an output shaft which is connected to a nylon gear 222 which is connected by toothed engagement 63 to nylon gear 224 which drives the peristaltic pump shaft 226. The motor 62a may be a 12 pole magneto-ceramic core motor which turns synchronously at 300 RPM if 60 cycle power is applied. Since the speed is low, it is possible to use a single pair of nylon gears to reduce the RPM to that required for the flow rates of 25 ml to 200 ml per minute with great ease and efficiency. By utilizing a large diameter shaft 226, a high concentricity is obtained with anti-reverse bearing 227 while excellent clutching action is obtained. Bearing 227 is a dual acting rolling-pin bearing with a built-in no-reverse clutching action which is required so that no possible reversing of the motor can take place, thus absolutely preventing return of all debrided material back into the eve or other body cavity. The bearing used is a standard Torrington type DC thin-cup, roller-clutch bearing and is highly effective. Thus, the advantages of low RPM is obtained with a few gears as is a positive noreverse feature not previously available.

A major breakthrough in a peristaltic pump design has been accomplished in the present invention and is one of great importance because we have discovered that the major disadvantages of peristaltic pumps of the prior art is that of the head spacing. In other words, if the spacing between the rotor 237 and the clamping head 250 is too small the peristaltic pump acts as a perfect shoe-type brake, overheating the motor and seriously wasting motor power; while, if the spacing is too great, the pump will not pump at all or pump only slowly, intermittently and inadequately.

We have discovered that by rotating the head 250 to an offset angle of 12° relative to the rotor center, as illustrated in FIG. 2 and by using a camming action at pivot point 236 that the head spacing can be uniquely adjusted—over the proscribed action area—of plus or minus 0.010 inches, thus, providing an adjustment for any variations in tubing size which heretofore can be a constant cause of trouble. Furthermore, an additional springing action is applied at 238 by the adjustment of a knob 239. A swivel joint 235 is provided for opening while 238 contains a spring around its enclosed shaft 241. The spacing between the head 250 and the rotor 237 can be accomplished by adjusting the cam 242 which is an eccentric cam. This cam 242 should be adjusted with the spring 238 uncompressed by turning the knob 239 until no pumping occurs with the tubing 228 is in place in the pump. Set screw 243 is then locked down to hold the eccentric cam 242 in position, then the knob 239 may be rotated to tighten the spring 238 so as to increase the pressure on the tubing gradually as the shaft 226 rotates. It will be observed that the pump will begin to take hold and the vacuum gauge needle will begin to bounce which will occur at a relatively low reading and frequency. Further turning of the knob 239 will cause the gauge's bouncing to gradually decrease and the gauge will begin a steady climb to a higher negative pressure; in other words, vacuum level. Putting slightly more pressure on the spring by turning the knob 239 still further and all bounciness of the gauge needle will completely disappear and a clean steady climb and negative-pressure will be achieved. One additional slight adjustment of about one-quarter turn and the gauge will be precisely set and the pump will be pumping evenly and solidly with a slight reserve pressure on it.

Observation of this action with the tubing in place will show that the spring 238 is causing the swing-head 250 to bounce upward and downward continuously as the rotor 237 is turning and the tubing is being alternately compressed by the five rollers 265a through e. The pulsating action is very smooth and no braking action exists. Furthermore, any solid debris coming into the tubing acts against the compression of spring 238 and passes easily through the pump. The secret of the success of the pump is in the 12° offset and the "bouncy" spring 238. The pump is silent and smooth operating at all speeds and is practically failure proof.

It is seen that the invention provides a novel medical machine and although it has been described with respect to preferred embodiments it is not to be so limited as changes and modifications may be made which are within the full intended scope as defined by the appended claims.

We claim as our invention:

1. A peristaltic pump comprising a frame member, a drive shaft, a rotor rotatably supported in said frame member on said drive shaft, a plurality of roller mounted on the outer surface of said rotor, a semicircular frame portion partially surrounding said rotor, a flexible tube mounted between said rotor and said semicircular frame member and said rollers engageable therewith, means for adjusting the spacing between said rotor and said semicircular frame portion, wherein said adjusting means comprises a pivot shaft attached to said frame on a radius from said drive shaft on an angle between zero and 30 degrees from where said tube enters the path of said rotor and one end of said semicircular frame supported on said pivot shaft, adjustable means mounted between the other end of said semicircular frame portion and said frame, and including an off center eccentric cam mounted between said pivot shaft and said frame member and means for selectively locking said cam in any desired position depending on headspacing required.

2. A peristaltic pump according to claim 1 wherein said adjustable means comprise a threaded bolt and a spring mounted between said threaded bolt and said other end of said semicircular frame portion so as to provide a bouncing action.

* * * * *